US010350325B2

(12) United States Patent
Remmers et al.

(10) Patent No.: US 10,350,325 B2
(45) Date of Patent: Jul. 16, 2019

(54) DISPOSABLE ABSORBENT ARTICLE AND A METHOD FOR MAKING THE SAME

(71) Applicant: H.B. FULLER COMPANY, St. Paul, MN (US)

(72) Inventors: Peter Remmers, Hamburg (DE); Thomas Wittkopf, Vogelsen (DE); Ursula Ruediger, Reppenstedt (DE); Carlos Briseno, St. Paul, MN (US)

(73) Assignee: H.B. Fuller Company, St. Paul, MN (US)

( * ) Notice: Subject to any disclaimer, the term of this patent is extended or adjusted under 35 U.S.C. 154(b) by 880 days.

(21) Appl. No.: 14/290,420

(22) Filed: May 29, 2014

(65) Prior Publication Data
US 2014/0358100 A1 Dec. 4, 2014

Related U.S. Application Data

(60) Provisional application No. 61/828,453, filed on May 29, 2013, provisional application No. 61/828,468, filed on May 29, 2013.

(51) Int. Cl.
A61L 15/24 (2006.01)
A61F 13/15 (2006.01)
A61F 13/539 (2006.01)
A61L 15/58 (2006.01)
C09J 123/10 (2006.01)
C08L 23/10 (2006.01)
A61F 13/49 (2006.01)
C09J 123/12 (2006.01)

(52) U.S. Cl.
CPC ........ A61L 15/24 (2013.01); A61F 13/15699 (2013.01); A61F 13/49009 (2013.01); A61F 13/539 (2013.01); A61L 15/585 (2013.01); C08L 23/10 (2013.01); C09J 123/10 (2013.01); C09J 123/12 (2013.01); A61F 2013/1591 (2013.01); A61F 2013/15121 (2013.01); A61F 2013/53908 (2013.01)

(58) Field of Classification Search
None
See application file for complete search history.

(56) References Cited

U.S. PATENT DOCUMENTS

| 4,037,601 | A | * | 7/1977 | Denkinger | A61F 13/2051 604/366 |
| 4,046,945 | A | * | 9/1977 | Baxmann | C09J 123/02 156/313 |
| 4,075,382 | A | * | 2/1978 | Chapman | A47K 10/16 156/219 |
| 4,100,922 | A | * | 7/1978 | Hernandez | A61F 13/49001 604/365 |
| 4,736,002 | A | * | 4/1988 | Allen | C08F 210/06 502/132 |
| 4,847,340 | A | * | 7/1989 | Allen | C08F 210/06 526/124.7 |
| 4,859,757 | A | * | 8/1989 | Pellon | C08F 210/06 526/124.7 |
| 4,937,299 | A | * | 6/1990 | Ewen | C08F 10/00 502/113 |
| 5,143,968 | A | * | 9/1992 | Diehl | A61L 15/58 428/349 |
| 5,149,741 | A |   | 9/1992 | Alper et al. | |
| 5,185,398 | A | * | 2/1993 | Kehr | C09D 123/02 524/504 |
| 5,218,071 | A | * | 6/1993 | Tsutsui | C08F 10/06 526/160 |
| 5,387,208 | A | * | 2/1995 | Ashton | A61F 13/534 604/358 |
| 5,475,075 | A | * | 12/1995 | Brant | C08F 210/16 526/160 |
| 5,539,056 | A | * | 7/1996 | Yang | C08L 23/10 525/240 |
| 5,669,894 | A | * | 9/1997 | Goldman | A61L 15/42 604/366 |
| 5,714,554 | A | * | 2/1998 | Sustic | C08F 210/06 526/125.3 |
| 5,723,546 | A | * | 3/1998 | Sustic | C08L 23/12 428/343 |
| 6,232,391 | B1 |   | 5/2001 | Sambasivam et al. | |
| 7,199,180 | B1 |   | 4/2007 | Simmons et al. | |
| 9,334,431 | B2 |   | 5/2016 | Hamann et al. | |
| 2002/0019507 | A1 | * | 2/2002 | Karandinos | C09J 123/10 526/348.2 |
| 2002/0123726 | A1 | * | 9/2002 | Zhou | B32B 5/02 604/366 |
| 2003/0096896 | A1 | * | 5/2003 | Wang | C09J 123/10 524/425 |
| 2005/0054779 | A1 | * | 3/2005 | Zhou | B32B 7/12 525/240 |
| 2006/0184146 | A1 | * | 8/2006 | Suzuki | A61F 13/535 604/358 |
| 2007/0135563 | A1 |   | 6/2007 | Simmons et al. | |
| 2009/0270825 | A1 | * | 10/2009 | Wciorka | A61F 13/495 604/367 |
| 2010/0029851 | A9 | * | 2/2010 | Jiang | C08F 10/06 525/191 |

(Continued)

FOREIGN PATENT DOCUMENTS

EP 1 788 058 5/2007
WO WO2009/100414 8/2009

(Continued)

OTHER PUBLICATIONS

H.B. Fuller Company, Duty of Candor Under 37 CFR 1.56, A Disposable Absorbent Article and a Method for Making the Same, May 2012-May 29, 2013.

Primary Examiner — Bradley H Philips
(74) Attorney, Agent, or Firm — Kristen Stone; Kristi Halloran

(57) ABSTRACT

Disclosed is a disposable absorbent article including two substrates; and an adhesive composition including a first polymer that is propylene-based and has a Mw of no greater than about 75,000, and a second polymer that is propylene-based and has a Mw of at least about 100,000, where the adhesive composition is used for at least two applications in the disposable absorbent article and is delivered via a molten bulk tank.

33 Claims, No Drawings

(56) References Cited

U.S. PATENT DOCUMENTS

| | | | |
|---|---|---|---|
| 2010/0305531 A1 | 12/2010 | Bach et al. | |
| 2011/0021102 A1 | 1/2011 | Inoue et al. | |
| 2011/0021103 A1* | 1/2011 | Alper | B32B 5/26 |
| | | | 442/329 |
| 2012/0328805 A1* | 12/2012 | Davis | B32B 7/12 |
| | | | 428/35.2 |
| 2013/0225752 A1* | 8/2013 | Tse | C08L 23/10 |
| | | | 524/505 |
| 2014/0134910 A1 | 5/2014 | Mansfield | |
| 2014/0199545 A1* | 7/2014 | Moriguchi | C09J 123/12 |
| | | | 428/349 |
| 2016/0121014 A1* | 5/2016 | Remmers | A61F 13/539 |
| | | | 604/365 |

FOREIGN PATENT DOCUMENTS

| | | |
|---|---|---|
| WO | WO2011/022523 | 2/2011 |
| WO | WO2012/129489 | 9/2012 |
| WO | WO2013/039261 | 3/2013 |
| WO | WO2013/039263 | 3/2013 |
| WO | WO2014/034916 | 3/2014 |

* cited by examiner

DISPOSABLE ABSORBENT ARTICLE AND A METHOD FOR MAKING THE SAME

This patent claims the benefit of or priority to U.S. provisional application 61/828,453 and U.S. provisional application 61/828,468 both filed on May 29, 2013.

BACKGROUND

Adhesives are often used to bond substrates together so as to maintain the two substrates in a fixed relation to each other. In the area of industrial adhesives, hot melt adhesives are commonly used to bond together a wide variety of articles including disposable absorbent articles comprising non-woven substrates e.g. adult incontinence products, disposable diapers, sanitary napkins, bed pads, puppy pads, medical dressings, etc.

There can be multiple hot melt adhesives used in the manufacture of a disposable absorbent article. For example, in the manufacture of a disposable diaper, adhesives are used in construction (e.g. bonding the backsheet to the nonwoven and optionally the absorbent pad), elastic attachment (e.g. bonding the elastic material to the backsheet in for example the leg or waist area), and for the core stabilization (e.g. applying an adhesive to the absorbent core to increase the strength of the core).

SUMMARY

In one aspect, the invention features a disposable absorbent article including a first substrate and a second substrate and an adhesive composition applied to at least one of the first or second substrates, said adhesive composition including a first polymer that is propylene-based and has a Mw of no greater than about 75,000, a second polymer that is propylene-based and has a Mw of at least about 100,000, where the propylene-based polymers have a polydispersity index of less than about 5, and where the adhesive composition is in at least two different applications in the disposable absorbent article.

In one embodiment, the adhesive composition has a static shear of no less than about 400 seconds. In another embodiment, the static shear is at least 20% greater than the static shear of NW1137. In still another embodiment, the adhesive composition comprises no greater than about 25% by weight plasticizer, or even no greater than about 20% by weight plasticizer. In a different embodiment, the adhesive composition comprises greater than about 20% by weight plasticizer.

In one embodiment, the second polymer is present at from about 2% to about 15% by weight, or even from about 3% to about 10% by weight. In another embodiment, the second polymer comprises greater than about 75% by weight propylene. In a different embodiment, the second polymer has a Mw of at least about 150,000. In one embodiment, the first polymer is a propylene homopolymer. Alternately, the first polymer is a propylene copolymer.

In one embodiment, the first polymer is present at greater than about 30% by weight. In another embodiment, the adhesive has a total polymer content of at least about 35% by weight.

In a different embodiment, the adhesive has a viscosity increase of less than about 10% when tested according to the Thermal Stability Test Method at a temperature of 150° C. In one embodiment, the adhesive further comprises a tackifying agent and a plasticizer.

In one embodiment the first polymer is present at from about 15% to about 50% by weight, the second polymer is present at from about 2% to about 15% by weight, and the plasticizer is present at less than about 20% by weight.

In another embodiment, the at least two applications are selected from the group consisting of construction, elastic attachment and core stabilization. Alternately, the at least two applications are construction and core stabilization. In one embodiment, the core of the absorbent disposable article is substantially free of cellulose.

In one embodiment, the disposable absorbent article is selected from the group consisting of an adult incontinence product, a sanitary napkin and a diaper. In another embodiment, the disposable absorbent article is a diaper.

In one aspect, the invention includes a method of applying an adhesive composition, the method including transferring a molten adhesive in a molten bulk tank to at least one disposable absorbent article assembly line within a manufacturing facility, the molten adhesive composition comprising a first polymer that is polypropylene-based and has a Mw of no greater than about 75,000, and a second polymer that is polypropylene-based and has a Mw of greater than about 100,000 wherein the propylene-based polymers have a polydispersity index of less than about 5; applying the molten adhesive composition in at least two different applications in the manufacture of the disposable absorbent article.

In another embodiment, the adhesive composition used in the method has an Initial Molten Gardner Color of no greater than about 3 and a viscosity increase of less than about 10% when tested according to the Thermal Stability Test Method at a temperature of 150° C. In a different embodiment, the two different applications are selected from the group consisting of construction, elastic attachment, and core stabilization. In one embodiment, the adhesive composition has a viscosity of less than about 10,000 cps when tested at around 150° C.

In another aspect, the invention covers a method of making a disposable absorbent article including obtaining an adhesive composition including a first polymer that is polypropylene-based and has a Mw of no greater than about 75,000, a second polymer that is polypropylene-based and has a Mw of greater than about 100,000, wherein the propylene-based polymers have a polydispersity index of less than about 5; applying the adhesive composition to a first substrate wherein the adhesive composition is supplied from a central molten bulk tank; and contacting the adhesive composition with a second substrate such that the first substrate is adhered to the second substrate through the adhesive composition, wherein the absorbent article further comprises a core which is substantially cellulose free and also comprises said adhesive composition.

GLOSSARY

In reference to the invention, these terms have the meanings set forth below:

Propylene-based refers to a polymer that comprises at least about 50% by weight propylene.

DETAILED DESCRIPTION

Applicants have discovered a hot melt adhesive that can be used for two or more of the adhesive applications in a disposable absorbent article. The olefin based adhesive has surprisingly good shear properties, low odor and better thermal stability than prior art olefin adhesives which enables delivery from a molten bulk tank.

Disposable Absorbent Article

The disposable absorbent article includes a nonwoven substrate and an adhesive composition. The adhesive composition is used for at least two different applications in the disposable absorbent article. The adhesive can be used for three applications in the disposable absorbent article.

The disposable absorbent article can be selected from the group consisting of adult incontinence products, disposable diapers, sanitary napkins, bed pads, puppy pads, and medical dressings.

The adhesive can be used for any two applications in the disposable absorbent article. Possible applications include but are not limited to construction (e.g., bonding the backsheet to the nonwoven and optionally, the absorbent pad), elastic attachment (e.g., bonding the elastic material to the backsheet in for example the leg or waist area), and for core stabilization (e.g. applying an adhesive to the absorbent core to increase the strength of the core).

Adhesive Composition

The adhesive composition is a hot melt adhesive. The adhesive can be a pressure sensitive adhesive. The adhesive composition can be light in color and can have good thermal stability. The adhesive can have an Initial Gardner Color after manufacturing of less than about 3, or even less than about 2. The adhesive has a viscosity change of no greater than about 20%, no greater than about 15%, or even no greater than about 10% when tested according to the Thermal Stability Test Method. The light color and good thermal stability make it possible to hold the adhesive in a molten bulk tank until it is needed for use.

The adhesive composition can have a static peel when tested according to the Static Peel Test that is greatly improved versus prior art olefin based hot melt adhesives currently on the market (NW1137 available from HB Fuller Company is used as a control). The Static Peel can be 15% greater than the static peel of NW1137, 20% greater than the static peel of NW1137, or even 50% greater than the static peel of NW1137.

The adhesive composition can have a static peel when tested according to the Static Peel Test of no less than about 65 seconds, no less than about 75 seconds, no less than about 100 seconds, or even from about 75 seconds to about 225 seconds.

The adhesive composition has low viscosity at application temperature. The viscosity can be no greater than about 10,000 cps at around 150° C., or even no greater than about 8,000 cps at around 150° C.

The adhesive composition has good shear properties when exposed to elevated temperatures. The light color, low viscosity and good shear properties make it possible to use the adhesive in more than one application in the manufacture of a disposable absorbent article.

Propylene-Based Polymers

The adhesive composition includes two different propylene-based polymers. The propylene-based polymers can be propylene homopolymers. Alternately, one or more of the two different propylene-based polymers can be copolymers with one or more other monomers (e.g. ethylene, butene, pentene, octene, etc.). The propylene-based polymers can be based entirely on olefins, i.e. do not contain any functional groups. The propylene-based polymers can comprise greater than 75% by weight propylene or even greater than 80% by weight propylene. The propylene-based polymers can have a polydispersity (Mw/Mn) of less than about 5, less than about 3, or even about 2. Useful propylene-based polymers can have a density of no greater than about 0.90, no greater than about 0.89, or even no greater than about 0.88. Useful propylene-based polymers include single-site (e.g. metallocene) catalyzed propylene-based polymers.

The weight average molecular weight of the first polymer is less than the weight average molecular weight of the second polymer.

The first polymer can have a weight average molecular weight (Mw) of less than about 75,000, less than about 60,000, less than about 50,000 or even between about 30,000 and about 70,000. The first polymer can be present in the adhesive composition in an amount of at least about 20% by weight, at least about 25% by weight, at least about 30% by weight, from about 15% to about 50% by weight, or even from about 25% to about 45% by weight. Useful commercially available first polymers include LICOCENE PP1602 and LICOCENE PP2602, propylene ethylene copolymers, both available from Clariant International Ltd. (Muttenz, Switzerland) and L-MODU X400S and L-MODU X600S, propylene homopolymers, available from Idemitsu Kosan Co., Ltd. (Japan).

The second polymer can have a molecular weight (Mw) of at least about 100,000, at least about 125,000, at least about 150,000, between about 125,000 and about 400,000, or even between about 150,000 and 250,000. The second polymer can be present in the composition in an amount of no greater than about 20%, no greater than about 15% by weight, no greater than about 8%, from about 2% by weight to about 15% by weight, or even from about 3% by weight to about 10% by weight. Useful commercially available second polymers include VISTAMAXX 6202 and VISTAMAXX 6102, propylene ethylene copolymers, available from ExxonMobil Chemical (Houston, Tex.) and VERSIFY 3300, a propylene ethylene copolymer, available from Dow Chemical Company (Houston, Tex.).

The total propylene-based polymer content of the adhesive can be at least about 20% by weight, at least about 25% by weight, at least about 30% by weight, at least about 35% by weight, or even from about 35% by weight to about 50% by weight.

Third Polymer

The composition can optionally include a styrenic block copolymer. The styrenic block copolymer can be hydrogenated. Useful hydrogenated styrene block copolymers include, e.g., styrene-ethylene/butadiene-styrene block copolymer, styrene-ethylene/propylene-styrene block copolymer, styrene-ethylene/ethylene/propylene-styrene block copolymer, and combinations thereof.

The styrenic block copolymer can have a styrene content of less than about 20% by weight, less than about 18% by weight, or even less than about 15% by weight. The styrene block copolymer can also have a Melt Flow when tested according to ASTM 1238 (230° C., 5 kg) of less than about 25 g/10 min, less than about 20 g/10 min, less than about 10 g/10 min, or even less than about 5 g/10 min.

Suitable hydrogenated styrene block copolymers are commercially available under a variety of trade designations including, e.g., the SEPTON series of trade designations from Kuraray Co. Ltd (Houston, Tex.) including, e.g., SEPTON S2063 and S2007 hydrogenated styrene-isoprene-styrene block copolymers, the KRATON G series of trade designations from Kraton Performance Polymers Inc. (Houston, Tex.) including, e.g., KRATON G 1645M, KRATON G 1657 styrene-ethylene/butdiene-styrene block copolymers.

The adhesive composition can include no greater than about 20% by weight, no greater than about 15% by weight, from about 2% to 20% by weight, or even from about 5% to 15% by weight of the third polymer.

Plasticizer

The adhesive composition can include a plasticizer. The plasticizer can be saturated (e.g. mineral oil, paraffinic oil, etc.) in order to improve heat stability for bulk handling. Suitable plasticizers include, e.g., naphthenic oils, paraffinic oils (e.g., cycloparaffin oils), mineral oils, phthalate esters, adipate esters, olefin oligomers (e.g., oligomers of polypropylene, polybutene, and hydrogenated polyisoprene), polybutenes, polyisoprene, hydrogenated polyisoprene, polybutadiene, benzoate esters, animal oil, plant oils (e.g. castor oil, soybean oil), derivatives of oils, glycerol esters of fatty acids, polyesters, polyethers, lactic acid derivatives and combinations thereof.

Useful commercially available plasticizers include CALSOL 550, naphthenic oil from Calumet Specialty Products Partners, LP (Indianapolis, Ind.), KAYDOL OIL, white mineral oil, from Sonneborn (Tarrytown N.Y.) PARAPOL polybutene from Exxon Mobil Chemical Company (Houston, Tex.), OPPANOL polyisobutylene from BASF (Ludwigsjhafen, Germany), KRYSTOL 550 mineral oil from Petrochem Carless Limited (Surrey, England) and PURETOL 15 mineral oil from Petro Canada Lubricants Inc. (Mississauga, Ontario).

The plasticizer is present in the adhesive composition in an amount no greater than about 25% by weight, no greater than about 20% by weight, no greater than about 18% by weight, greater than about 20% by weight, from about 5% to about 30% by weight, or even from about 10% to about 20% by weight.

Tackifying Agent

The adhesive can include a tackifying agent. The tackifying agent can be at least partially hydrogenated in order to improved stability for bulk handling. The tackifying agent can be fluid or solid at room temperature. Suitable classes of tackifying agents include, e.g., aromatic, aliphatic and cycloaliphatic hydrocarbon resins, mixed aromatic and aliphatic modified hydrocarbon resins, aromatic modified aliphatic hydrocarbon resins, and hydrogenated versions thereof; terpenes, modified terpenes and hydrogenated versions thereof; natural rosins, modified rosins, rosin esters, and hydrogenated versions thereat low molecular weight polylactic acid; and combinations thereof. Examples of useful natural and modified rosins include gum rosin, wood rosin, tall oil rosin, distilled rosin, hydrogenated rosin, dimerized rosin and polymerized rosin. Examples of useful rosin esters include e.g., glycerol esters of pale wood rosin, glycerol esters of hydrogenated rosin, glycerol esters of polymerized rosin, pentaerythritol esters of natural and modified rosins including pentaerythritol esters of pale wood rosin, pentaerythritol esters of hydrogenated rosin, pentaerythritol esters of tall oil rosin, and phenolic-modified pentaerythritol esters of rosin.

Useful tackifying agents are commercially available under a variety of trade designations including, e.g., hydrocarbon resins under the ESCOREZ series of trade designations from Exxon Mobil Chemical Company (Houston, Tex.), including ESCOREZ 5400 and ESCOREZ 5600, aliphatic hydrocarbon resins under the EASTOTAC series of trade designations from Eastman Chemical (Kingsport, Tenn.), including EASTOTAC H-100R and EASTOTAC H-100L, and hydrocarbon resins under the WINGTACK series of trade designations from Cray Valley HSC (Exton, Pa.), including WINGTACK 86, WINGTACK EXTRA, and WINGTACK 95 and aliphatic hydrocarbon resins under the PICCOTAC and aromatic hydrocarbon resins under the KRISTALEX series of trade designations from Eastman Chemical Company (Kingsport, Tenn.) including, e.g., PICCOTAC 8095 and KRISTALEX 3100.

The adhesive composition can include at least about 10% by weight, at least about 20% by weight, from about 5% by weight to about 60% by weight, from about 10% by weight to about 50% by weight, or even from about 10% by weight to about 40% by weight tackifying agent.

Wax

The adhesive composition can include a wax. Useful classes of wax include, e.g., paraffin waxes, microcrystalline waxes, high density low molecular weight polyethylene waxes, by-product polyethylene waxes, polypropylene waxes, Fischer-Tropsch waxes, oxidized Fischer-Tropsch waxes, functionalized waxes such as acid, anhydride, and hydroxy modified waxes, animal waxes, vegetable waxes (e.g. soy wax) and combinations thereof. Useful waxes are solid at room temperature and preferably have a Ring and Ball softening point of from 50° C. to 170° C. Useful waxes are commercially available from a variety of suppliers including polypropylene and polyethylene waxes available under the EPOLENE N and C series of trade designations from Westlake Chemical Corporation (Houston, Tex.) including e.g. EPOLENE N-21, a polyethylene wax and polypropylene and polyethylene waxes available under the LICOCENE series of trade designations from Clariant International Ltd. (Muttenz, Switzerland) including e.g. TP LICOCENE PP 6102, a polypropylene wax.

The adhesive composition can include no greater than about 10% by weight, no greater than about 5% by weight, from about 1% by weight to about 10% by weight, or even from about 1% to about 5% by weight wax.

Additional Components

The adhesive composition optionally includes additional components including, e.g., stabilizers, antioxidants, additional polymers (e.g. styrenic block copolymers, amorphous poly-alpha olefins, polyethylene copolymers), adhesion promoters, ultraviolet light stabilizers, corrosion inhibitors, colorants (e.g., pigments and dyes), fillers, surfactants, wetness indicators, superabsorbents and combinations thereof.

Useful antioxidants include, e.g., pentaerythritol tetrakis [3,(3,5-di-tert-butyl-4-hydroxyphenyl)propionate], 2,2'-methylene bis(4-methyl-6-tert-butylphenol), phosphites including, e.g., tris-(p-nonylphenyl)-phosphite (TNPP) and bis(2,4-di-tert-butylphenyl)4,4'-diphenylene-diphosphonite, di-stearyl-3,3'-thiodipropionate (DSTDP), and combinations thereof. Useful antioxidants are commercially available under a variety of trade designations including, e.g., the IRGANOX series of trade designations including, e.g., IRGANOX 1010, IRGANOX 565, and IRGANOX 1076 hindered phenolic antioxidants and IRGAFOS 168 phosphite antioxidant, all of which are available from BASF Corporation (Florham Park, N.J.), and ETHYL 702 4,4'-methylene bis(2,6-di-tert-butylphenol). When present, the adhesive composition preferably includes from about 0.1% by weight to about 2% by weight antioxidant.

Disposable Absorbent Article

The adhesive composition can be applied to (i.e. such that it is in direct contact with) or incorporated in a variety of substrates within the disposable absorbent article including, e.g., films (e.g., polyolefin (e.g., polyethylene and polypropylene) films), release liners, porous substrates, cellulose substrates, sheets (e.g., paper, and fiber sheets), paper products, woven and nonwoven webs, fibers (e.g., synthetic polymer fibers and cellulose fibers), elastics and tape backings.

The adhesive composition is also useful in a variety of applications and constructions including, e.g., disposable absorbent articles including, e.g., disposable diapers, adult incontinence products, sanitary napkins, medical dressings (e.g., wound care products) bandages, surgical pads, pet training pads (e.g. puppy pads) and meat-packing products, and components of absorbent articles including, e.g., an absorbent element, absorbent cores, impermeable layers (e.g., backsheets), tissue (e.g., wrapping tissue), acquisition layers and woven and nonwoven web layers (e.g., top sheets, absorbent tissue).

The adhesive composition is useful on substrates made from a variety of fibers including, e.g., natural cellulose fibers such as wood pulp, cotton, silk and wool; synthetic fibers such as nylon, rayon, polyesters, acrylics, polypropylenes, polyethylene, polyvinyl chloride, polyurethane, and glass; recycled fibers, and various combinations thereof.

Various application techniques can be used to apply the composition to a substrate including, e.g., slot coating, spraying including, e.g., spiral spraying and random spraying, screen printing, foaming, engraved roller, extrusion and meltblown application techniques.

Methods of Making a Disposable Absorbent Article

The adhesive composition is thermally stable, low in viscosity and has good heat resistance in a shear mode. These properties make it useful for multiple applications in the construction of a disposable absorbent article. Additionally, the adhesive composition has performance breadth enabling it to perform in at least two different applications in the same absorbent article. Such different applications may require different application methods or adhesive add-on levels. As used herein, "at least two different applications" refers to the adhesive adhered to at least two different areas of the absorbent article to serve at least two different purposes in the absorbent article. For example, the adhesive could be used in various construction applications, as a core stabilizer, and/or in elastic attachments.

The adhesive can be used for construction applications. In a typical construction application in the manufacture of a disposable absorbent article, a body fluid impermeable backsheet is bonded to a nonwoven substrate. The adhesive may also be used to bond at least one additional layer or material selected from the group consisting of absorbents, tissues, elastomeric materials, superabsorbent polymers, and combinations thereof. The body fluid impermeable backsheet is typically a polyolefin film (e.g. polyethylene, polypropylene, ethylene vinyl acetate, ethylene copolymer, etc.).

The adhesive can be used to contain and/or provide strength to the absorbent core of a disposable absorbent article (i.e. as a core stabilization adhesive). The absorbent core can include many different materials including natural cellulose fibers (e.g. wood pulp, fibers, cotton, fluff, etc.) and superabsorbent polymers (e.g. polyacrylates). In some disposable absorbent articles, the absorbent core is substantially cellulose free. In a cellulose free core, the absorbent core consists of adhesive and superabsorbent polymer.

The adhesive can be used for elastic attachment applications, for example in diapers, which include bonding elastic material to either the leg and/or waist area. The elastic material can be bonded to polyolefin (e.g. polyethylene, polypropylene, etc.) films or nonwoven substrates to result in creep resistant gathers.

The invention has superior thermal stability compared to prior art olefin based adhesives. This makes it useful in an application system wherein the adhesive is stored in a molten bulk tank to be supplied to at least one assembly line for use in more than one application on the same article.

The adhesive can be held in a molten bulk tank at a temperature below the application temperature of the adhesive. As the adhesive is needed, it can be conveyed in heated hoses to the appropriate melt tanks where it is heated to the required temperature prior to application.

The adhesive can be used as the construction adhesive and the core adhesive in the same article.

The invention includes a method of adhesive application including providing a molten adhesive in a molten bulk tank wherein the molten adhesive comprises a first polymer that is polypropylene-based and has a Mw of no greater than about 75,000, and a second polymer that is polypropylene-based and has a Mw of greater than about 100,000; transferring the molten adhesive from the molten bulk tank to at least one assembly line within a manufacturing facility; and using the molten adhesive in at least two different applications in the manufacture of a disposable absorbent article.

The high shear resistance of the adhesive makes it particularly useful for strengthening the core. The invention includes a method of making a disposable absorbent article including obtaining an adhesive composition including a first polymer that is polypropylene-based and has a Mw of no greater than about 75,000; a second polymer that is polypropylene-based and has a Mw of greater than about 100,000; applying the composition to a first substrate using an application system wherein the adhesive is supplied from a central molten bulk tank in molten form; and applying a second substrate on top of the composition, such that the composition forms a bond between the first and second substrate where the absorbent core is substantially cellulose free and also comprises said adhesive composition.

The invention will now be described by way of the following non-limiting examples. All parts, ratios, percents and amounts stated in the Examples are by weight unless otherwise specified.

EXAMPLES

Test Procedures

Test procedures used in the examples and throughout the specification, unless stated otherwise, include the following.

Viscosity Test Method

Viscosity is determined in accordance with ASTM D-3236 entitled, "Standard Test Method for Apparent viscosity of Adhesives and Coating Materials," (Oct. 31, 1988), using a Brookfield Thermosel viscometer Model RVDV 2 and a number 27 spindle. The results are reported in centipoise (cps).

Thermal Stability

A hot melt composition is held at 300° F. (149° C.) for periods of 24 hours, 48 hours, 72 hours, and 96 hours. Viscosity and/or Molten Gardner Color of the aliquots can then be tested. Thermal stability is recorded as the change in viscosity over 96 hours and is calculated as a percent change according to the following formula:

$$((\text{final viscosity} - \text{initial viscosity})/\text{initial viscosity})*100$$

Molten Gardner Color

The adhesive is tested (in the molten state) to determine Gardner color by comparing the color of the sample against the Gardner Color Standards as set forth in ASTM D-1544. The comparison is made using a Gardner Delta Comparator equipped with an Illuminator available from Pacific Scientific (Bethesda, Md.).

Static Peel Test

Adjust hot melt applicator and laminator to recommended settings for the desired adhesive. The goal is to make an application of one uniform adhesive spiral measuring a width of approximately 12.7 mm (0.5 inches). Adjustments can be made based on the type of adhesive or application. The adhesive was applied to the treated side of a polyethylene film (DH-284 PE White available from Clopay Plastic Products Company, Augusta, Ky.) at a coat weight of 6.0 gram/m² and nipped to the nonwoven (UNIPRO 45 available from Midwest Filtration Company, Cincinnati, Ohio) substrate.

Bonds are made with the test adhesive/s and NW1137 as a control.

Once the pattern width and desired adhesive coat weight has been achieved run several feet of material then insert sheets of paper in to nip to make the sample starting points (about 10 paper sheets), take care to insert the paper 90° square to the lamination this will insure a straight bond line to start the peel. Leave each of the adhesive laminations on the roll until they are ready to be tested, in approximately 24 hrs.

Unroll the samples and cut test coupons 100 mm long in the machine direction 50 mm of paper tag to start the peel and 50 mm of bonded substrate. Then cut the test coupons 40 mm wide in the cross-machine, with the middle spiral in the center. When cutting the test coupons be sure to cut the coupons in such a way as to maintain a straight and square line at the test start point. Prepare 3 samples for each adhesive. Roll and staple the tag end of the unbonded poly film then roll and staple the tag end of the unbonded nonwoven. This will allow a secure place to hold the test samples in place during the static peel.

Place the test coupons and the 100 g test weights in a 37° C. oven for at least 30 min to equilibrate. To begin the test attached the poly film end of the test coupon to the top of the rack in the oven and then carefully attach the 100 g weight to the nonwoven end of the test sample when the weight is released start the timer, stop the timer when the poly and nonwoven are completely separated and the weight falls. Repeat the test alternating between the control adhesive and the test adhesive until at least 3 replicates of each adhesive have been tested.

Report the average time to failure of the test sample/s and NW1137 in seconds, plus any additional descriptive and pertinent information such as substrate failure or any variations in the application or test method.

TABLE 1

Polymer Properties

|  | L-MODU X400S | L-MODU X600S | LICOCENE PP1602 | VISTA-MAXX 6202 | VERSIFY 2300 |
|---|---|---|---|---|---|
| Supplier | Idemitsu Kosan Co., Ltd. | Idemitsu Kosan Co., LTd. | Clariant | Exxon Mobil Chem. Co. | Dow Chemical Company |
| Polymer Type | PP Homo-Polymer | PP Homo-Polymer | PP/PE copolymer | PP/PE Copolymer | PP/PE copolymer |
| Ethylene content (wt %) | 0 | 0 |  | 15 |  |
| Mw | 45,000 | 70,000 | 47,600 | 184,000 |  |
| Mw/Mn | 2 | 2 | 4.6 | 2.1 | 2-3 |
| Mass Flow Rate (g/10 min) |  |  |  | 18 (230° C., 2.16 kg) | 2.0 (230° C., 2.16 kg) |
| Density | .87 | .87 | .87 | .861 | .867 |

TABLE 2

Examples

|  | Comp. 1* | Comp. 2* | Example 1 | Example 2 | Example 3 | Example 4 | Example 5 |
|---|---|---|---|---|---|---|---|
| L-MODU S-400 |  |  | 32 | 35 | 23 | 17 |  |
| LICCOCENE PP1602 |  |  |  |  |  |  | 32 |
| VISTAMAXX 6202 |  |  | 8 | 5 | 10 | 11 | 8 |
| ESCOREZ 5400 |  |  | 34.8 | 34.8 | 39.8 | 39.8 | 34.8 |
| CALSOL 550 |  |  | 20 | 20 | 22 | 25 |  |
| KRYSTOL 550 |  |  |  |  |  |  | 20 |
| EPOLENE N-21 |  |  | 3 | 3 | 3 | 5 | 3 |
| IRGANOX 1076 |  |  | 0.2 | 0.2 | 0.2 | 0.2 | 0.2 |
| COEXTRUSION COATING |  |  | 2 | 2 | 2 | 2 | 2 |
| Molten Viscosity at 300° F. (148.9° C.) (cps) | 3150 | 4800 | 6825 | 4650 | 6400 | 4500 | 8075 |
| Initial Gardner Color | 3.0 | 2.5 | 1 | 1 | 1 | 1 | 1 |
| Thermal Stability (% change in viscosity) | −25% | +15% | +7.3% | +14.0% | +6.5% | +4.4% | +18.3% |
| Static Peel (seconds) | 201 | 72 | 89 | 124 | 67 | 39 | 108 |

TABLE 2-continued

| | Examples | | | | | |
|---|---|---|---|---|---|---|
| | Comp. 1* | Comp. 2* | Example 1 | Example 2 | Example 3 | Example 4 | Example 5 |
| Static Peel as compared to NW1137 | | | +23.6% | +72.2% | −6.9% | −45.8% | +50.0% |

The coextrusion coating contains the following in the stated weight percentages:
ESCOREZ 5415 - Exxon Mobil Chemical Company (Houston, Texas) 34.8%
KRATON G1652 - Kraton Performance Polymers Inc. (Houston, Texas) 25%
SHELL MICROWAX HMP - Shell Deutschland Oil GmbH 39.6%
IRGANOX 1072 0.6%
The adhesive compositions of Examples 1-4 were prepared by combining and mixing the components in the percentages set forth in Table 2 in a sigma blade mixer operating at 177° C.
The adhesive composition of Example 5 can be prepared by combining and mixing the components in the percentages set forth in Table 2 in a sigma blade mixer operating at 177° C.
*Comparative 1 is HL1358LO, an SIS (styrene-isoprene-styrene) based hot melt adhesive commercially available from HB Fuller Company
*Comparative 2 is NW1137, an ethylene-octene based hot melt adhesive commercially available from HB Fuller Company Other embodiments are within the claims.

What is claimed is:

1. A disposable absorbent article comprising:
a first substrate and a second substrate; and
an adhesive composition applied to at least one of the first or second substrates, said adhesive composition comprising:
from about 15% to about 45% of a first polymer that is single-site catalyzed and propylene-based and has a Mw of from about 30,000 to about 75,000; and
from about 2% to about 15% of a second polymer that is propylene-based and has a Mw from about 100,000 to about 400,000, and wherein the second polymer has a density of no greater than 0.89, and
wherein the adhesive composition is used in at least two different applications in the disposable absorbent article, the at least two different applications selected from the group consisting of construction, elastic attachment, and core stabilization.

2. The article of claim 1 wherein the adhesive composition further comprises plasticizer.

3. The article of claim 1 wherein the adhesive composition comprises greater than about 20% by weight plasticizer.

4. The article of claim 1 wherein said second polymer is present at from about 3% to about 10% by weight of the adhesive composition.

5. The article of claim 1 wherein said second polymer comprises greater than about 75% by weight propylene.

6. The article of claim 1 wherein the said second polymer has a Mw of at least about 150,000.

7. The article of claim 1 wherein the first polymer is a propylene homopolymer.

8. The article of claim 1 wherein the first polymer is a propylene copolymer.

9. The article of claim 1 wherein the first polymer is present at greater than about 30% by weight of the adhesive composition.

10. The article of claim 1 wherein the adhesive composition has a total polymer content of at least about 35% by weight.

11. The article of claim 1 wherein the at least two applications are construction and core stabilization.

12. The disposable absorbent article of claim 1 wherein said disposable absorbent article is selected from the group consisting of an adult incontinence product, a sanitary napkin and a diaper.

13. An absorbent article comprising:
an adhesive; and
a substantially cellulose free absorbent core comprising the adhesive and superabsorbent polymers;
wherein the adhesive secures at least a portion of the substantially cellulose free absorbent core to a material of the absorbent article; and wherein the adhesive comprises:
from about 15% to about 45% of a first polymer that is single site catalyzed and propylene-based and has a Mw from about 30,000 to about 75,000; and
from about 2% to about 15% of a second polymer that is propylene-based and has a Mw from about 100,000 to about 400,000, and wherein the second polymer has a density of no greater than 0.89.

14. The article of claim 13, wherein the material comprises a nonwoven substrate.

15. The article of claim 13, wherein the adhesive comprises no greater than about 20% by weight of the adhesive of plasticizer and from about 3% to about 10% by weight of the adhesive of the second polymer.

16. The article of claim 13, wherein the first propylene-based polymer has a polydispersity index from about 2 to about 5, and the second propylene-based polymer has a polydispersity index from about 2 to about 5.

17. The article of claim 13, wherein the second polymer comprises greater than about 75% propylene by weight of the second polymer.

18. The article of claim 13, wherein the second polymer has a Mw from about 150,000 to about 400,000.

19. The article of claim 13, wherein the first polymer is present at greater than about 30% by weight of the adhesive, and wherein the adhesive has a total polymer content of at least about 35% by weight of the adhesive.

20. The article of claim 13, wherein the adhesive is a core stabilization adhesive.

21. The article of claim 13, wherein the adhesive is a core stabilization adhesive and a construction adhesive.

22. The article of claim 13, wherein the first polymer has a Mw from about 30,000 to about 50,000 and the second polymer has a Mw from about 125,000 to about 400,000.

23. The article of claim 13, wherein the material of the absorbent article is a portion of the absorbent core.

24. An absorbent article comprising:
an adhesive; and
a cellulose free absorbent core comprising the adhesive and superabsorbent polymers;

wherein the adhesive is configured to join at least a portion of the cellulose free absorbent core to a portion of the absorbent article; and wherein the adhesive comprises:

from about 15% to about 45% of a first polymer that is single-site catalyzed and propylene-based and has a Mw from about 30,000 to about 75,000;

from about 2% to about 15% of a second polymer that is propylene-based has a Mw from about 100,000 to about 400,000, and wherein the second polymer has a density of no greater than 0.89.

25. The article of claim 24, wherein the portion of the absorbent article comprises a nonwoven substrate.

26. The article of claim 24, wherein the adhesive comprises no greater than about 20% by weight of the adhesive of plasticizer and from about 3% to about 10% by weight of the adhesive of the second polymer.

27. The article of claim 24, wherein the second polymer comprises greater than about 75% propylene by weight of the second polymer and wherein the second polymer has a Mw from about 150,000 to about 400,000.

28. The article of claim 24, wherein the first polymer is present at greater than about 30% by weight of the adhesive, and wherein the adhesive has a total polymer content of at least about 35% by weight of the adhesive.

29. The article of claim 24, wherein the adhesive is a core stabilization adhesive.

30. The article of claim 24, wherein the adhesive is a core stabilization adhesive and a construction adhesive.

31. The article of claim 24, wherein the first polymer has a Mw from about 30,000 to about 50,000 and the second polymer has a Mw from about 125,000 to about 400,000.

32. The article of claim 13 wherein the adhesive further comprises a plasticizer.

33. The article of claim 24 wherein the adhesive further comprises a plasticizer.

* * * * *